United States Patent [19]
Snyder et al.

[11] Patent Number: 5,110,076

[45] Date of Patent: May 5, 1992

[54] ADJUSTABLE MULTIPOLE SUPPORT STAND FOR MEDICAL FLUIDS

[75] Inventors: Stephen J. Snyder, Van Nuys; John L. Wilson, Bishop, both of Calif.

[73] Assignee: Cal-Surgical, Inc., Bishop, Calif.

[21] Appl. No.: 640,823

[22] Filed: Jan. 14, 1991

[51] Int. Cl.⁵ .............................................. A47G 29/00
[52] U.S. Cl. ..................................... 248/125; 248/408
[58] Field of Search ............ 248/125, 129, 124, 123.1, 248/408, 409, 407, 188.5, 297.3; 211/205

[56] References Cited

U.S. PATENT DOCUMENTS

| | | | |
|---|---|---|---|
| 3,554,585 | 1/1971 | Sorenson | 248/408 X |
| 3,807,574 | 4/1974 | Lanza | 248/125 X |
| 4,332,378 | 6/1982 | Pryor | 211/205 X |
| 4,725,027 | 2/1988 | Bekanich | 248/125 |
| 4,744,536 | 5/1988 | Bancalari | 248/125 |
| 4,832,294 | 5/1989 | Eidem | 248/129 X |
| 4,867,406 | 9/1989 | Lengacher | 248/409 |
| 4,905,944 | 3/1990 | Jost | 248/129 X |

Primary Examiner—J. Franklin Foss
Attorney, Agent, or Firm—Kelly, Bauersfeld & Lowry

[57] ABSTRACT

An improved adjustable multipole support stand is provided wherein each of a plurality of support poles is individually adjustable to a desired height. The stand generally comprises a plurality of vertically oriented support poles mounted in a parallel array about an upright main or center post and adapted for vertical sliding movement between raised and lowered positions. Spring loaded trigger assemblies carried by the support poles include locking pins registrable with vertically spaced notches in the center post to permit individual height adjustment of each support pole. The uppermost end of each support pole includes a hook or is otherwise suitably adapted to support a medical fluid container such as a bag of intravenous fluid or the like.

20 Claims, 3 Drawing Sheets

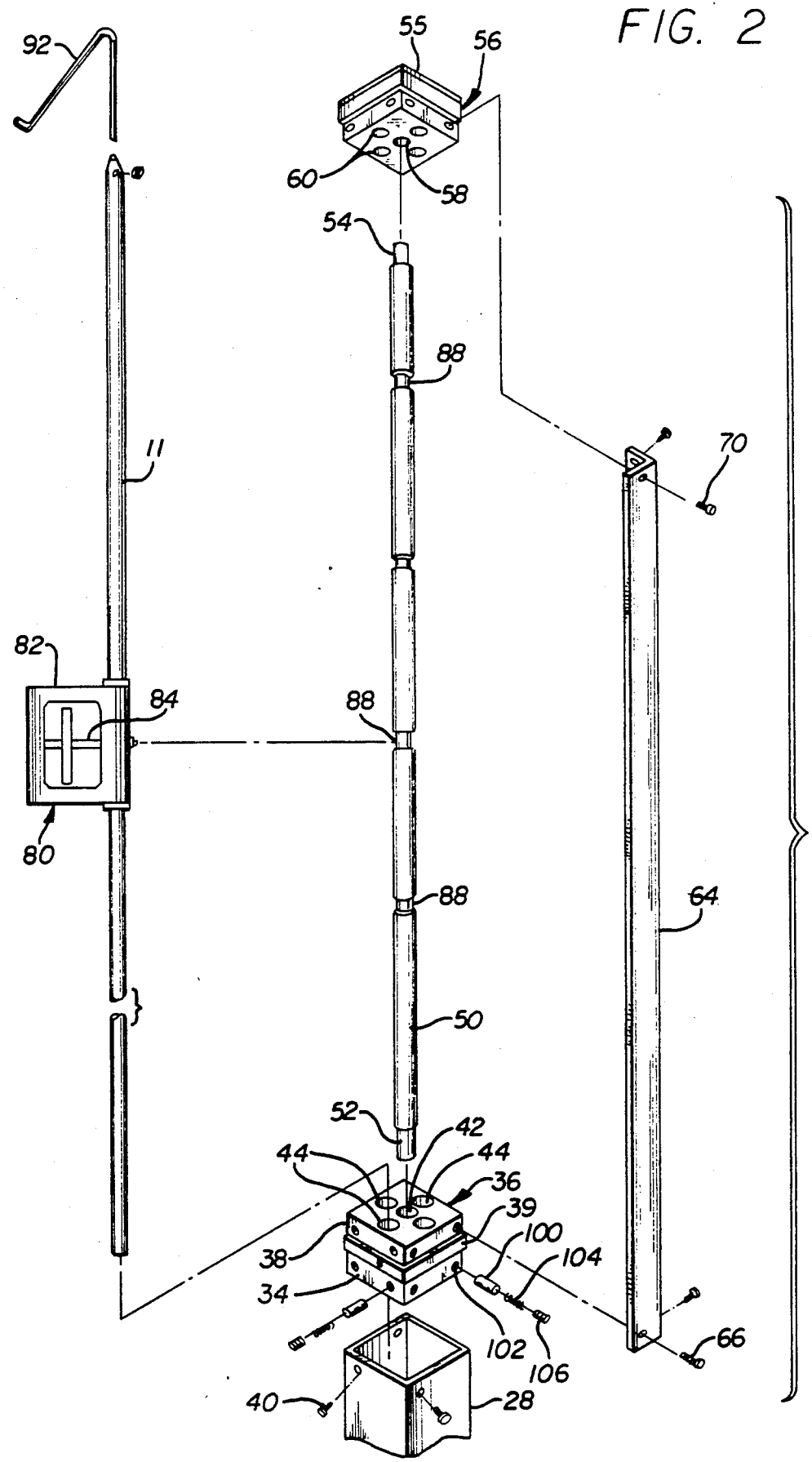

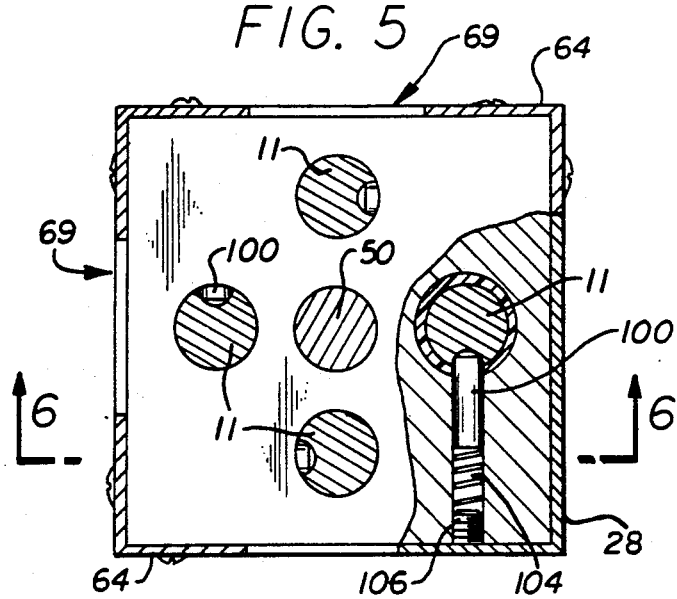
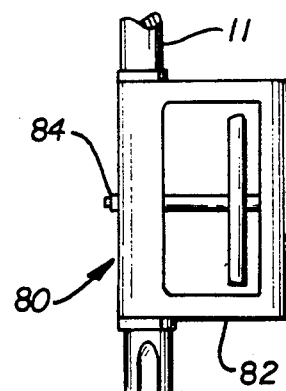
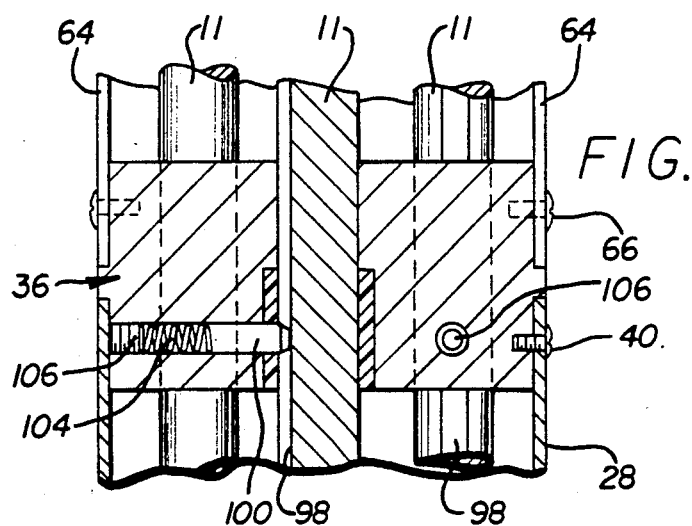
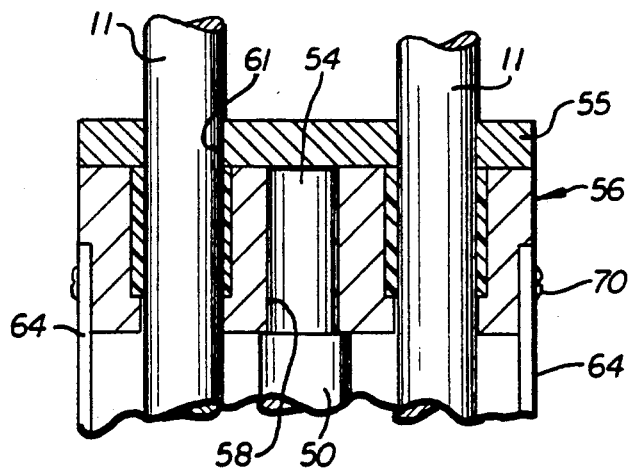

ADJUSTABLE MULTIPOLE SUPPORT STAND FOR MEDICAL FLUIDS

BACKGROUND OF THE INVENTION

This invention relates generally to improvements in support stands of the type used in surgical and other medical procedures to support medical fluids such as irrigation and/or infusion fluids to be administered to a patient. More particularly, this invention relates to an irrigation stand which has a multiplicity of individually adjustable support poles for holding a corresponding plurality of fluids at selected vertical positions.

Medical stands of the type used to support irrigation and/or infusion fluids are generally well-known in the medical arts. Such stands are typically constructed in the form of an upright pole supported by castered legs to accommodate rapid yet mobile deployment at patient bedside. One or more hooks are usually provided at the top of the stand so that a bag or bags of medical fluid can be hung therefrom in an elevated position. The vertical height of the stand and thus the vertical position of the fluid-containing the bag is often adjustable to regulate the rate of fluid administration to the patient.

In some medical treatment regimens, it is necessary or desirable to suspend multiple fluid-containing bags which may contain different fluids at a convenient location near the patient. For example, in many arthroscopic surgical procedures, simultaneous administration of multiple fluids is required, wherein it may be necessary or desirable to support these fluids at different vertical elevations. In the past, this has normally required a different support stand for each different fluid, with the resultant multiple stands occupying excessive space and potentially interfering with the surgical procedure. Alternately, modified support stands having multiple support hooks have been proposed, but these devices have not satisfactorily facilitated fluid support at individually selected vertical positions.

There exists, therefore, a significant need for an improved fluid support stand adapted for supporting multiple infusion and irrigation fluids and the like at individually selected vertical positions. The present invention fulfills these needs and provides further related advantages.

SUMMARY OF THE INVENTION

In accordance with the invention, an improved adjustable multipole support stand is provided with a plurality of support poles adapted to support medical fluids at individually selected vertical positions. The support stand generally comprises a castered frame which supports a main center post in an upright orientation within a surrounding array of vertically oriented support poles adapted for vertical sliding movement between raised and lowered positions. Lock means are provided cooperatively on the support poles and the center post to selectively and releasably lock the support poles in individually selected positions.

More specifically, in accordance with the preferred form of the invention, the frame of the improved support stand comprises a hollow lower base section extending upwardly from a plurality of outwardly radiating legs having caster wheels mounted thereon. A main guide block is mounted onto an upper end of the base section and defines a plurality of vertically open ports for slidably receiving the multiple support poles. The center post projects upwardly from the main guide block and is connected at its upper end to a cap block which also defines vertically open ports for slidably receiving the support poles. Accordingly, the support poles are individually slidable between raised and lowered positions along individual vertical axes defined by the ports formed in the main guide and cap blocks. A trigger assembly on each support pole includes a retractable spring loaded locking pin engageable with a selected one of a plurality of vertically spaced notches in the center post to releasably lock each support pole in an individually selected vertical position. A hook or the like at the upper end of each support pole facilitates mounting thereon of a bag filled with a medical fluid.

In accordance with further features of the invention, the lower ends of the support poles include a vertically elongated groove. Spring loaded tracking pins or the like carried by the main guide block extend into these support pole grooves to prevent pole rotation in the course of use and/or movement between the raised and lowered positions.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 2 is an exploded perspective view of an upper section of the support stand of FIG. 1;

FIG. 4 is an enlarged side elevation view of a lower portion of one of the support poles;

FIG. 5 is a horizontal section taken generally on the line 5—5 of FIG. 1, and showing construction details of a main guide block;

FIG. 6 is a vertical section taken generally on the line 6—6 of FIG. 5; and

FIG. 7 is a vertical section taken generally on the line 7—7 of FIG. 1.

DETAILED DESCRIPTION OF THE PREFERRED EMBODIMENT

Figure 1:
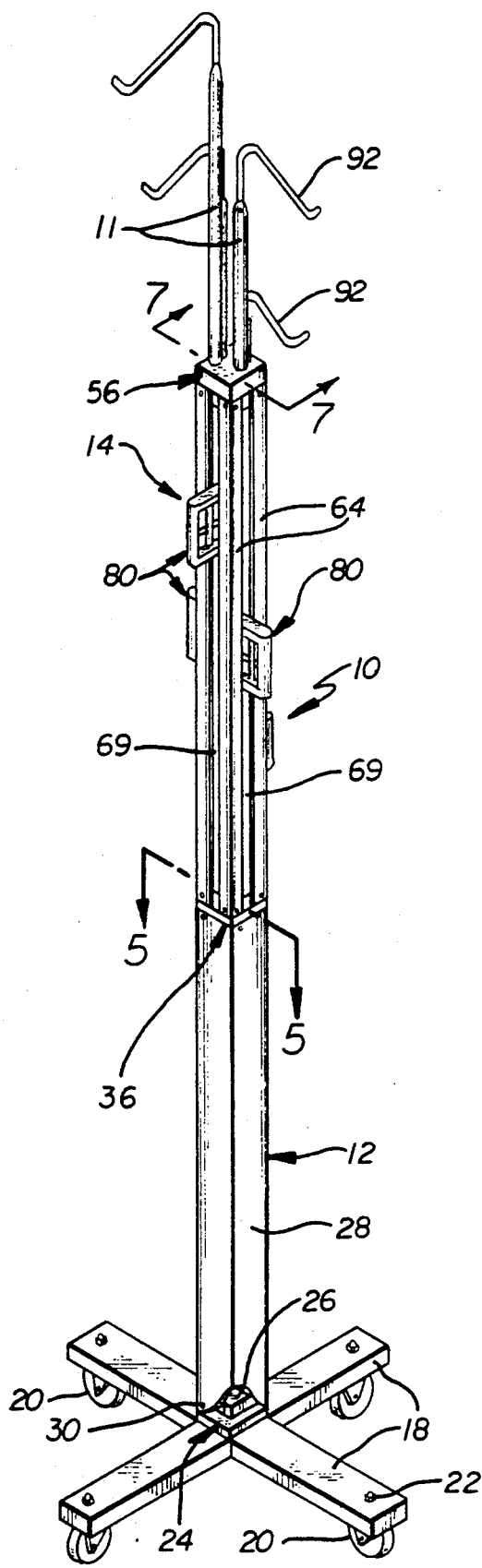
FIG. 1 is a perspective view, partially in vertical section, illustrating an adjustable multipole support stand embodying the novel features of the invention.

As shown in the exemplary drawings, an adjustable multipole support stand referred to generally in FIG. 1 by the reference numeral 10 is provided for use in supporting multiple bags (not shown) or the like containing medical fluids, such as intravenous or irrigation fluids and the like. The medical fluids are supported upon a plurality of upright support poles 11 adapted for individual vertical positional adjustment.

The multipole support stand 10 of the present invention provides a compact and easily manipulated device for supporting medical fluids in an organized manner and at individually selected vertical positions. The invention is thus particularly suited for use at patient bedside or in a surgical environment wherein administration of multiple medical fluids is or may become desirable. The individual support poles 11 are quickly and easily adjusted to the selected vertical positions for use, or are otherwise lowered to an out-of-the-way position retracted substantially into the frame structure of the support stand.

As shown best in FIG. 1, the support stand frame structure generally comprises a lower base section 12 which cooperates with an upper adjustment section 14 to support the support poles 11 for sliding movement in a vertical direction between raised and lower positions. The base section 12 includes a plurality of legs 18 which extend outwardly from a common base block 24. The legs 18 can be formed as individual elements although they would most commonly be formed by crossing two elements to create the generally X-shaped configuration. The outer end of each leg 18 is appropriately connected to a caster wheel 20 by means of a nut 22 or the like. The base block 24 may be securely affixed to the legs by means of bolts (not shown), or in some instances may be welded thereto. A vertically extending base housing 28 of hollow square cross section is received over an upper portion 26 of the base block 24 and extends upwardly therefrom. A plurality of screws 30 are provided to extend through the lower end of the base housing 28 to attach said base housing 28 to the base block 24.

The upper end of the base housing 28 provides a support seat for a lower portion 34 of a main guide block 36 (FIG. 2) and is secured thereto by means of a plurality of screws 40. The guide block 36 further includes an upper portion 38 which is separated from the lower portion 34 by a expanded ridge 39 extending over and generally coextensive with the outside surface geometry of the base housing 28. Importantly, the main guide block 36 defines a central hole 42 surrounded by a plurality of four ports 44, all of which are formed to extend along parallel vertical axes.

A main or center post 50 has a reduced diameter lower end 52 for seated reception into the central hole 42 in the main guide block 36. This center post 50 forms the primary frame structure of the adjustment section 14, and further includes a reduced diameter upper end 54 for seated reception into a central hole 58 formed in an upper cap block 56. As shown best in FIG. 2, the cap block 56 also defines a plurality of vertically oriented pole ports 60 provided in respective alignment with the four pole ports 44 in the main guide block 36. A cap plate 55 (FIGS. 2 and 7) may be mounted on top of the cap block 56 to close the upper extent of the central hole 58, with the cap plate having additional pole ports 61 in respective alignment with the pole ports 60.

A plurality of four corner braces 64 are also provided to interconnect the main guide block 36 and the cap block 56. These corner braces 64 are each formed with a generally L-shaped cross section and are secured to the guide block 36 and to the cap block 56 by means of screws 66 and 70, respectively, or the like. When installed, the corner braces cooperatively define a vertically elongated slot 69 at each of the four sides of the adjustment section 14. These vertical slots 69 permit access to the support poles 11 for adjustment purposes, as will be described in more detail.

The support poles 11 are provided in a number corresponding with the number of aligned port pairs 44 and 60 formed respectively in the main guide and cap blocks 36 and 56. These support poles 11 are slidably received within the port pairs for sliding motion along their respective vertical axes between the raised and lowered positions. In a lowered position, the uppermost end of the support pole 11 extends a short distance above the cap block 56, and a lowermost end projects downwardly through the main guide block 36 within the base housing 28 to a position at or near the lower base block 24. Conversely, in a raised position, the upper end of the support pole is disposed substantially above the cap block 56, with the lower pole end disposed at or slightly below the main guide block 36.

Figure 3:
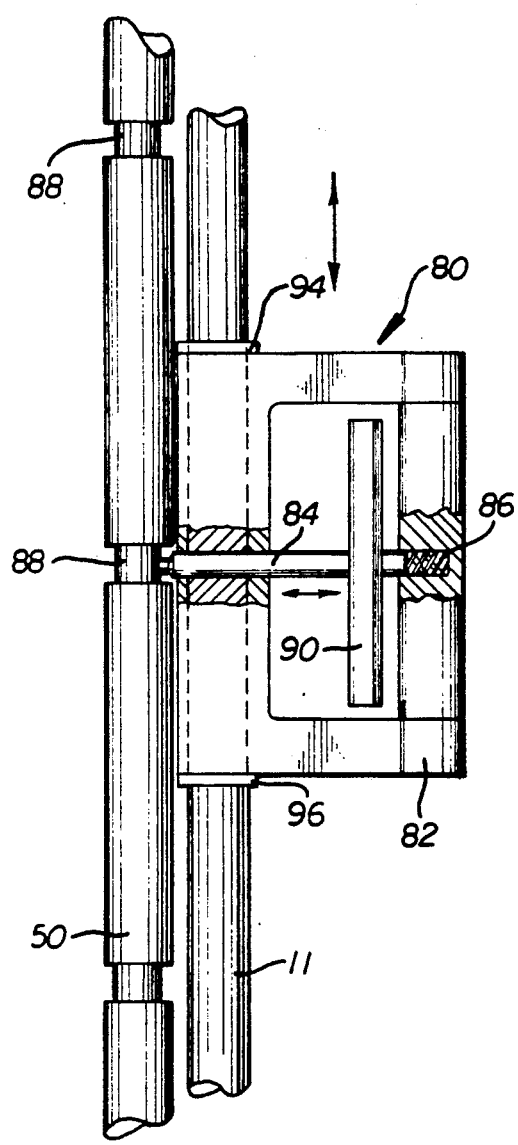
FIG. 3 is an enlarged side elevation view, partially in vertical section, of the support stand to show locking means associated with each of the plurality of support poles.

Each support pole 11 has a trigger assembly 80 mounted thereon for use in manually raising or lowering the pole, and in releasably locking the pole in the selected vertical position of adjustment. As viewed in FIGS. 2-4, each trigger assembly comprises a narrow profile handle 82 which is suitably attached to the associated pole 11 and extends outwardly through the associated slot 69 for manual access at one side of the stand. An inwardly directed locking pin 84 is carried by the handle 82 and is biased by a spring 86 in a direction toward the center post 50. The pin 84 is sized for reception into a selected one of a plurality of vertically spaced notches 88 formed along the center post 50 to releasably lock the pole 11 in a selected and individually adjustable vertical position. A trigger bar 90 is attached to the locking pin 84 and is manually grasped to retract the pin from the center post 50 when vertical pole adjustment is desired.

Accordingly, in use, the vertical position of each support pole 11 can be adjusted quickly and easily by appropriate manipulation of the locking pin 84 associated therewith. More particularly, retraction of the locking pin 84 associated with a selected pole 11 permits the pole to be raised or lowered as desired to orient the upper end thereof at a selected vertical position. A hook 92 (FIGS. 1 and 2) at the upper end of the pole provides a convenient support structure for supporting a medical fluid container, such as a bag of intravenous or irrigation fluid. Rubber stops 94 and 96 (FIG. 3) on the handle 82 are conveniently provided to abut the adjacent cap and guide blocks 56 and 36 when the pole is raised or lowered, respectively, to upper or lower end limit positions.

In accordance with further aspects of the invention, each support pole 11 may be equipped with antirotation means to prevent pole rotation about the vertical axis thereof. As viewed in FIGS. 5 and 6, this antirotation means comprises an elongated vertical groove 98 formed along a lower extent of the support pole. The grooves 98 in the support poles 11 are oriented to receive a respective tracking pin 100 mounted within a small bore 102 formed in the main guide block 36. In the preferred form, these tracking pins 100 are urged by springs 104 which react against set screws 106 in the bores 102 to extend into the associated pole groove 98, and thereby prevent support pole rotation throughout a range of vertical adjustment.

A wide variety of modifications and improvements to the adjustable multipole support stand of the present invention will be apparent to those skilled in the art. For example, as depicted throughout the accompanying drawings, bushings may be utilized within the various pole ports for smooth sliding pole motion between the raised and lowered positions. Accordingly, no limitations on the present invention is intended by way of description herein and the accompanying drawings, except as set forth in the appended claims.

What is claimed is:

1. A multipole support stand for medical fluids and the like, comprising:

a plurality of elongated and generally vertically oriented support poles each including support means disposed generally at an upper end thereof for supporting a medical fluid container;

a frame structure including an upright center post and having means for supporting said poles in a generally vertically oriented parallel array for sliding movement of said poles along parallel axes between raised and lowered positions; and lock means for releasably and individually locking each of said poles in a selected vertical position of adjustment relative to said frame structure, each of said lock means engageable with said center post.

2. The multipole support stand of claim 1 wherein said support means at the upper end of each of said poles comprises a hook.

3. The multipole support stand of claim 1 further including caster means for supporting said frame structure for rolling movement over a floor surface.

4. The multipole support stand of claim 1 wherein said lock means comprises a plurality of trigger assemblies carried respectively by said poles and each including a manually retractable lock pin adapted for releasable engagement into a selected one of a plurality of vertically spaced notches formed in said frame structure.

5. The multipole support stand of claim 4 wherein each of said trigger assemblies includes a manually accessible handle for manually moving said poles individually between said raised and lower positions.

6. The multipole support stand of claim 4 wherein said lock pin of each of said trigger assemblies is spring loaded for normal movement toward a locked position engaged into a selected one of said notches in said frame structure.

7. The multipole support stand of claim 4 wherein said upright center post has said notches formed therein, and slide means at the upper and lower ends for supporting said poles in generally parallel array about said center post for sliding movement between said raised and lowered positions, said trigger assemblies on said poles having said lock pins oriented to extend generally radially inwardly toward said center post for respective reception into selected individual ones of said notches.

8. The multipole support stand of claim 7 wherein each of said trigger assemblies includes a handle extending from the associated support pole in a direction radially outwardly from said center post.

9. The multipole support stand of claim 7 wherein the number of said support poles is four.

10. The multipole support stand of claim 7 further including means for preventing rotation of said support poles about their respective axes.

11. The multipole support stand for medical fluids and the like, comprising:

a frame structure including a hollow and generally vertically oriented base section, a guide block at an upper end of said base section, a center post extending vertically from said guide block and having a plurality of vertically spaced stops formed therein, and a cap block at an upper end of said center post;

a plurality of support poles disposed generally in a parallel and vertically extending array about said center post, each of said support poles having upper and lower ends received slidably through a respective aligned pair of pole ports formed in said guide and cap blocks to permit individual sliding movement of each of said support poles along its vertical axis between raised and lowered positions, with the upper end of each support pole being disposed above said cap block and the lower end of each support pole being disposed below said guide block and within the hollow interior of said base section; and lock means including a plurality of retractable lock pins carried respectively by said support poles for releasable engagement with individually selected ones of said stops on said center post.

12. The multipole support stand of claim 11 wherein said lock means further includes spring means for biasing said lock pins toward engagement with said stops.

13. The multipole support stand of claim 12 wherein said stops are defined by a plurality of vertically spaced notches formed in said center post.

14. The multipole support stand of claim 11 further including a plurality of castered legs supporting said base section for rolling movement.

15. The multipole support stand of claim 11 wherein said frame structure further includes brace members connected between said guide and cap blocks in a position generally circumscribing said support poles and defining a plurality of vertically elongated slots disposed respectively adjacent to and aligned with said support poles, and further wherein said lock means includes a plurality of trigger assemblies mounted respectively on said support poles and each including a handle projecting outwardly from the associated one of said support poles and further through the associated one of said vertical slots to a manually accessible position, each of said handles including trigger means for manually retracting the associated one of said lock pins.

16. The multipole support stand of claim 11 wherein each of said support poles has an elongated groove formed therein, and further including a plurality of tracking pins on said frame structure and received respectively into said support pole grooves to prevent support pole rotation.

17. A multipole support stand for medical fluids and the like, comprising:

a plurality of elongated and generally vertically oriented support poles each including support means disposed generally at an upper end thereof for supporting a medical fluid container;

a frame structure including an upright center post having a plurality of vertically spaced notches formed therein and slide means at the upper and lower ends of said center post for supporting said poles in generally parallel array about said center post for sliding movement of said poles along parallel axes between raised and lowered positions;

lock means for releasably and individually locking each of said poles in a selected vertical position of adjustment relative to said frame structure, said lock means comprising a plurality of trigger mechanisms carried respectively by said poles and each including a manually retractable lock pin oriented to extend generally radially inwardly toward said center post adapted for releasable engagement into a selected one of said notches formed in said center post.

18. The multipole support stand of claim 17 wherein each of said trigger assemblies includes a handle extending from the associated support pole in a direction radially outwardly from said center post.

19. The multipole support stand of claim 17 wherein the number of support poles is four.

20. The multipole support stand of claim 17 further including means for preventing rotation of said support poles about their respective axes.

* * * * *